(12) United States Patent
Heden et al.

(10) Patent No.: US 6,649,001 B2
(45) Date of Patent: Nov. 18, 2003

(54) METHOD AND AN ARRANGEMENT FOR PRODUCING BASIC FASTENER TAB MATERIAL, SUCH BASIC STARTING MATERIAL, AND FASTENER TABS

(75) Inventors: Anna Heden, Vallda (SE); Robert Kling, Skene (SE); Urban Nilsson, Kungälv (SE); Jose-Maria Mansisidor, Mölnlycke (SE)

(73) Assignee: SCA Hygiene Products AB, Gothenburg (SE)

(*) Notice: Subject to any disclaimer, the term of this patent is extended or adjusted under 35 U.S.C. 154(b) by 135 days.

(21) Appl. No.: 09/812,857

(22) Filed: Mar. 21, 2001

(65) Prior Publication Data

US 2001/0036786 A1 Nov. 1, 2001

Related U.S. Application Data

(60) Provisional application No. 60/197,609, filed on Apr. 18, 2000.

(30) Foreign Application Priority Data

Mar. 21, 2000 (SE) .......................................... 0000937-3

(51) Int. Cl.[7] .............................................. B32B 31/18
(52) U.S. Cl. ........................ 156/160; 156/163; 156/164; 156/229; 156/250; 156/252; 156/253; 156/268; 156/269; 442/327; 442/328

(58) Field of Search ................................ 156/73.1, 160, 156/163, 164, 229, 250, 251, 252, 253, 268, 269; 442/327, 328; 428/223

(56) References Cited

U.S. PATENT DOCUMENTS

| 5,057,097 A | 10/1991 | Gesp |
| 5,759,317 A | 6/1998 | Justmann |
| 6,391,013 B1 * | 5/2002 | Suzuki et al. .......... 604/385.27 |

FOREIGN PATENT DOCUMENTS

| WO | 95/05140 | 2/1995 |
| WO | 99/48455 | 9/1999 |

* cited by examiner

*Primary Examiner*—Elizabeth M. Cole
(74) *Attorney, Agent, or Firm*—Young & Thompson

(57) ABSTRACT

A method of producing basic starting material for the manufacture of fastener tabs comprises the steps of: stretching a first sheet of elastic material in a first direction; applying a second and a third sheet of material onto respective opposite sides of the first sheet; fastening the three material sheets together in at least two mutually separated zones that extend parallel with each other in one direction perpendicular to the first direction; dividing the first sheet in each region between two zones along a line that lies between the zones, whereby the first sheet in each region between the zones contracts to a non-stretched state, and thereafter fastening the sheets together in each region between the zones.

5 Claims, 5 Drawing Sheets

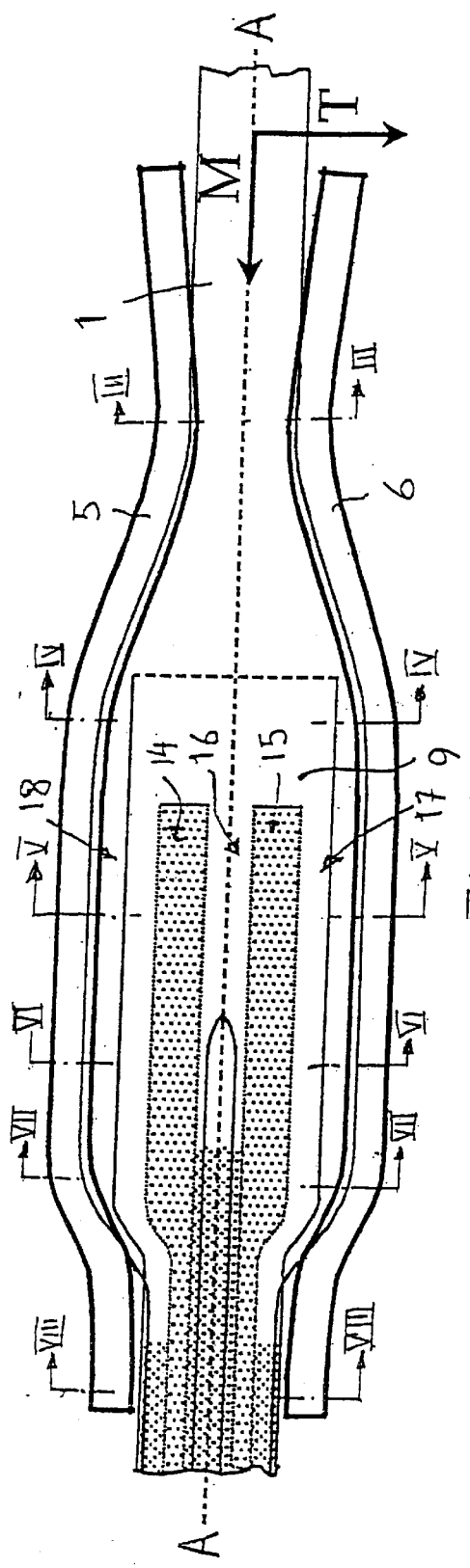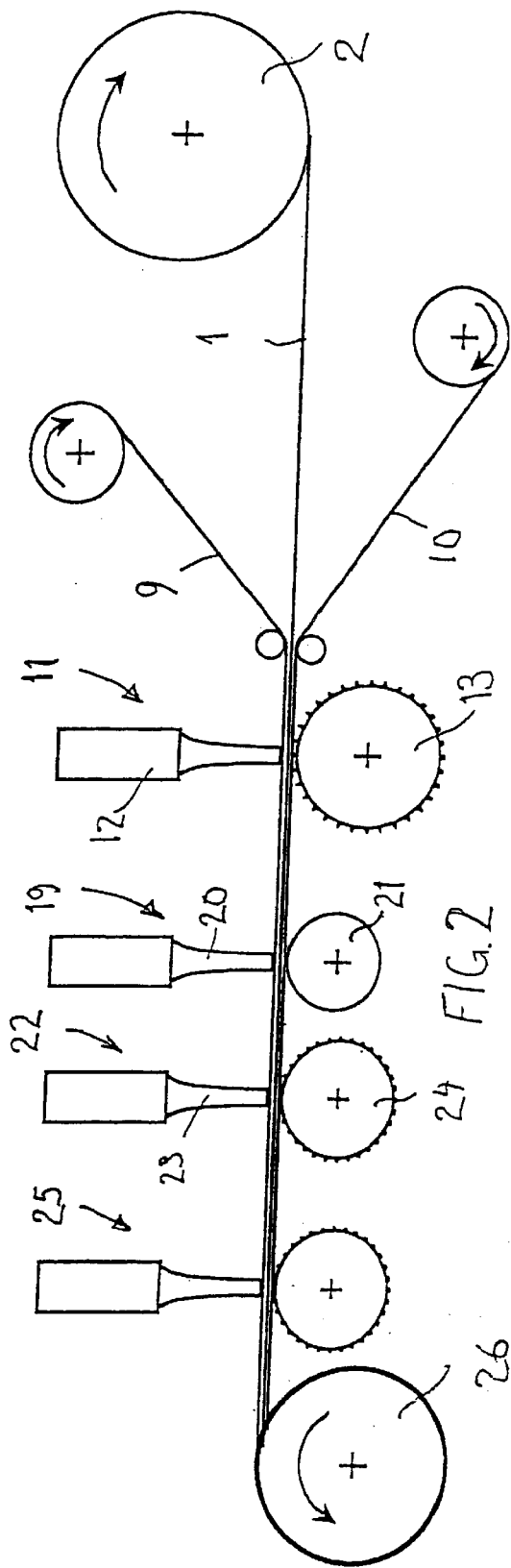

METHOD AND AN ARRANGEMENT FOR PRODUCING BASIC FASTENER TAB MATERIAL, SUCH BASIC STARTING MATERIAL, AND FASTENER TABS

FIELD OF INVENTION

The present invention relates to a method and to an arrangement for producing basic starting material for the production of fastener tabs that are intended to fasten together the side portions of absorbent articles, such as diapers or like-articles that include a front part, a back part and an intermediate crotch part, so that the article will have a pants-like configuration. The invention also relates to such basic starting material and to a fastener tab produced from such material.

BACKGROUND OF THE INVENTION

Absorbent article fastener tabs used to fasten together the side portions of articles so that the article will have a pants-like configuration when worn are known in many different varieties. For instance, the tabs may be of a mechanical type that includes hooks of the touch-and-close fastener type or some like type, as described in EP-A1-0 235 014, for instance. Fastener tabs of this type, however, are expensive and difficult to apply at fast speeds in the manufacture of absorbent articles. Such tabs have therefore had limited use. WO-A1-95/05140 describes a fastener tab manufacturing method which is said to avoid these problems.

Other types of fastener devices that are more suited for application at high speeds are known to the art. For instance, it is known to provide a diaper with pressure-sensitive tape for fastening the diaper around the waist of a wearer, therewith fastening the front and back side of the diaper together to obtain a pants-like configuration. These tapes are often made of paper material and are therefore usually relatively rigid. These tapes are also often provided with some form of protective film that must be removed prior to use.

Elastic fastener devices are also known in the present context. For instance, U.S. Pat. No. 3,800,796 describes a disposable diaper that includes semi-elastic fastener tabs. The fastener tabs may comprise elastic material that forms an elastic zone surrounded by non-elastic material that forms two non-elastic zones, or may alternatively comprise solely elastic material that has been made non-elastic at its edge regions in some suitable manner. One of these non-elastic zones of the fastener tabs is fastened to the diaper and the other is provided with an adhesive substance, for instance.

TECHNICAL PROBLEMS

One problem resides in the ability of producing both left-hand and right-hand fastener tabs simultaneously, which is desirable since pairs of left-hand and right-hand fastener tabs are often fastened simultaneously to mutually sequential absorbent article blanks in the continuous manufacture of such articles. Furthermore, it shall be possible to produce absorbent articles provided with such fastener tabs at high production rates. Difficulties may be experienced in applying glue and other adhesive substances.

The fastener tabs must also be soft, partially air permeable and must not chafe the skin of the wearer.

Furthermore, it is desirable that elastic fastener devices will include a "stop function" that has a distinct stop which "informs" the user or the carer when the elastic part has been stretched to a maximum, i.e. includes casing material that prevents further stretching of the elastic sheets or layers. This can be achieved with stretched elastic fastened to a non-elastic casing material. Alternatively, the casing material can be pleated and fastened to a smooth elastic material, which may be either in a stretched or a relaxed state.

Against this background of the aforesaid problems, a preferred method has been a laminating method in which the elastic is stretched and the casing materials are smooth, and in which the casing materials are joined together, suitably by heat welding or ultrasound welding.

EP-A1-0 494 941 describes a method of producing an elastic material, by joining two sheets of non-stretchable material that enclose a stretched elastic sheet, through the medium of perforations in the elastic sheet. This document also discloses that zones of different elastic properties can be produced through the medium of different perforation patterns and that non-elastic zones can also be produced, wherein the non-elastic zones are parts that were originally elastic but that have been "killed" by intensive heat treatment or ultrasound welding. The resultant non-elastic zones are relatively dense, although they are air-permeable to some extent. Furthermore, the intensive treatment has a negative effect on the casing materials, which tend to become hard. The desired smooth surface is lost and the hard edges that are formed are very liable to chafe the wearer's skin when coming into contact therewith. Further examples of similar elastic material are found in WO-A1-92/15444, for instance.

It is difficult to pleat casing materials prior to being fastened to the elastic material, because of the high precision required. This difficulty is more pronounced at high manufacturing rates. The application of glue becomes difficult. When the materials are not thermally miscible, problems also occur in heat sealing processes.

There are thus problems which known technology has been unable to solve.

The above problems are essentially avoided completely by the present invention. The object of the invention is to provide a method and arrangement for producing basic starting material for the production of fastener tabs that have different degrees of stretchability in different directions and that are intended for fastening absorbent articles around the wearer's waist, and that can be produced in pairs at high production rates, and with which the use of adhesive agents can be limited. The fastener tabs shall also fulfil the requirement of softness, shall be air permeable and not cause chafing of the skin.

SUMMARY OF THE INVENTION

These objects are achieved in accordance with the invention with a method of producing basic starting material for the production of fastener tabs which are intended to join together the side-parts of the front and back portions of absorbent articles that include a front part, a back part and an intermediate crotch part so as to impart a pants-like configuration to said article, said method being characterised by the steps of stretching a first sheet of elastic material in a first direction;

applying a second and a third sheet of material on respective opposite sides of the first sheet;

fastening the three sheets of material together in at least two mutually separate zones that extend parallel to each other in a second direction perpendicular to said first direction;

dividing the first sheet in each region between two zones along a line that lies between said zones, wherewith the first sheet in each region between two zones contracts to a non-stretched or relaxed state, and thereafter fastening the three sheets of material together in each region between two zones.

In one preferred embodiment of the invention, the sheets of material are fastened together in each region between two zones in which the second and third sheets are fastened to the first sheet with said sheet in a stretched state and with the first sheet stretched in said zones.

In one alternative, the first sheet of material may be caused to contract to an unstretched state prior to the sheets being fastened together in each region between two zones, in which the second and third sheets are fastened to the first sheet with said sheet in a stretched state.

In one preferred embodiment of the invention, the first, second and third sheets of material are fastened together in two edge regions that extend in said second direction and that extend in said first direction outwardly of the nearest zone, in which the second and third sheets are fastened to the first sheet with said sheet in a stretched state subsequent to having caused said first sheet to contract to an unstretched state in the zones in which the second and third sheets have been fastened to the first sheet with said sheet in a stretched state.

Division of the first sheet in each region between two zones in which the second and third sheets are fastened to the first sheet with said sheet in a stretched state is effected by providing a line of perforations in the first sheet, wherein the spacing between said perforations is so small that the contracting force in the stretched first sheet is sufficient to pull the first sheet apart in the region between two mutually sequential perforations.

The invention also relates to an arrangement for the continuous production of basic starting material for the manufacture of fastener tabs that are intended to join the side-parts of the front and rear portions of absorbent articles that include a front part, a rear part and an intermediate crotch part, so as to impart a pants-like configuration to said article, said arrangement being characterised by means for advancing a first web of elastic material through said arrangement in one feed direction; means for stretching the first web transversely to the feed direction; means for applying a second and a third web of material onto respective opposite sides of said first web; means for fastening the combined webs together in at least two mutually separated zones that extend parallel with one another in said feed direction; means for dividing the first web in each region between two zones in which the three webs are fastened together with the first web in a stretched state, along a line that lies between said zones, wherein the first sheet of material in each region between two zones contracts to an unstretched or relaxed state; and means for fastening the webs together subsequent to the division of the first web in each region between two zones in which the three webs are fastened together with the first web in a stretched state.

According to one preferred embodiment, the arrangement includes means for bringing the stretched first web to an unstretched state, and downstream means in the feed direction for fastening the three webs together in the edge regions that extend in the feed direction outwardly of the transversely outermost zones in which the three webs of material are fastened together with the first web in a stretched state.

The means for bringing the stretched first web of material to an unstretched or relaxed state are preferably located downstream of the means for fastening the webs together in each region between two zones in which the three webs are fastened together with the first web in a stretched state, subsequent to having divided said first web. Alternatively, said means may be located immediately downstream of said means for dividing the first web of material in each region between two zones in which the three webs are fastened together with the first web in a stretched state.

The means for fastening said webs together will preferably have the form of an ultrasound welding unit or a heat welding unit. It is also possible to use different types of means for the different fastening operations. The means used to fasten the three webs together, with the first web in a stretched state, may alternatively have the form, of a gluing unit.

The means for dividing the first web in each region between two zones in which the three webs are fastened together with the first web in a stretched state, along a line that lies between said zones, may comprise a perforating device that perforates the first web. In the preferred embodiment, the perforating device is an ultrasound unit adapted to perforate the first web of material and to fasten the second and third webs together through the holes or openings created in the first web in said perforating process.

The invention also relates to a basic starting material for the production of fastener tabs which together function to fasten together the side-parts of an absorbent article that includes a front part, a rear part and an intermediate crotch part, so as to impart to the article a pants-like configuration, wherein the basic starting material has a length and a width, characterised in that said basic starting material includes at least two elastic zones that extend in the longitudinal direction of said material and that are mutually separated transversely by an intermediate non-elastic zone.

In one preferred embodiment, the elastic material extends from the elastic zones slightly into each non-elastic zone and the ratio between the transverse extension of the elastic zones in a maximum stretched state and in a relaxed state is smaller than or equal to the ratio of the transverse extension of the intermediate non-elastic zone to the sum of the transverse extension of those pieces of elastic material that extend into said zone.

The elastic zones include a layer or sheet of elastic material which is mounted in a stretched state between two sheets of material and fastened thereto, either directly or indirectly, said two sheets extending over each elastic and non-elastic zone. By "fastened directly" is meant that the sheets, or layers, are directly fastened to each other as by gluing or ultrasound welding for instance, whereas by "fastened indirectly" is meant that the two sheets or layers are fastened together via perforations in the intermediate sheet, in the manner described in the aforesaid EP-A1-0 404 941. At least one of the two sheets of material between which an elastic sheet is mounted in the elastic zones is comprised of a generally non-stretchable material, preferably a nonwoven material that will conveniently include thermoplastic fibres. In one advantageous variant, the two sheets of material between which an elastic sheet is mounted in the elastic zones are comprised of nonwoven material and both have mutually the same weight per unit area. In one preferred embodiment, both of said sheets are comprised of nonwoven material and have mutually different weights per unit area, wherewith one has a weight per unit area of 5–50 g/m$^2$ while the other has a weight per unit area of between 10–80 g/m$^2$. In one particularly preferred variant, at least one of the nonwoven sheets or layers is a spunbond nonwoven. Each elastic zone includes a sheet of elastic film, elastic foam, elastic net or a laminate that includes at least one elastic component.

The invention also relates to a fastener tab which is intended to be fastened to one side part of an absorbent article that includes a front part, a rear part and an intermediate crotch part, so as to join mutually coacting side-parts of the front and rear part of the article and therewith give the article a pants-like configuration, wherein the fastener tab has a user end and a manufacturer end and is characterised in that it includes a layer of elastic material which is fastened in a stretched state to two layers or sheets of generally unstretchable material, either directly or indirectly; in that the two unstretchable layers extend beyond the elastic layer so as to form an unstretchable end part; in that the elastic layer extends in a relaxed state slightly into the unstretchable end-part; and in that fastener means are mounted in the unstretchable end-part in the user end of one of the two unstretchable layers.

In one preferred embodiment, the unstretchable layers or sheets are comprised of nonwoven material of mutually different weights per unit area, and the fastener means are attached to the outside of the nonwoven sheet that has the lowest weight per unit area.

Finally, the invention relates to an absorbent article, such as a diaper or an incontinence protector, which is characterised by including a fastener tab according to the above.

Basic starting material produced in accordance with the method and by means of the inventive arrangement thus enables left-hand and right-hand fastener tabs to be produced at a high production rate while obtaining a soft and comfortable product.

An important feature of the fastener tabs and the basic starting material is that the elastic zone presents a clear stop in a maximum extended or stretched position. Furthermore, the non-elastic zone outwardly of the elastic zone on the fastener tabs and between the elastic zones of the basic starting material respectively shall be smooth so as to facilitate application of fastener elements, such as male fastener elements or female fastener elements in said zone. The basic starting material produced is continuous. A continuous web of material is mainly beneficial from a process/technical aspect, although not necessarily so.

Further preferred embodiments will be apparent from the detailed description of preferred embodiments given below with reference to the accompanying drawings.

BRIEF DESCRIPTION OF THE DRAWINGS

The invention will now be described in more detail with reference to the accompanying drawings, in which FIG. 1 illustrates schematically and from above an embodiment of an inventive arrangement for producing basic fastener tab material, although the ultrasound welding unit used in the arrangement is not shown in this Figure;

FIG. 2 is a partially cut-away view from one side of the arrangement shown in FIG. 1, and shows schematically the ultrasound welding unit used in the arrangement;

DETAILED DESCRIPTION OF PREFERRED EMBODIMENTS

Figure 3:
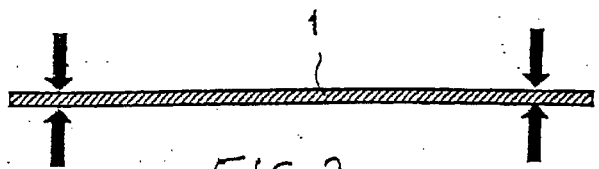
FIGS. 3–8 are cross-sectional views taken on the lines III—III to and including VIII—VIII in FIG. 1.

FIGS. 1–10 illustrate schematically one embodiment of an inventive arrangement of devices for producing basic starting material for the manufacture of elastic fastener tabs intended for attachment to absorbent articles, such as diapers or incontinence protectors, so as to impart a pants-like configuration to the article when the article is donned by a wearer.

A first web 1 of elastic material is fed from a storage reel 2 in the feed direction M and moved into the inventive arrangement. Upon entry into said arrangement, the edges of the web 1 are firmly clamped by a clamping device 5, 6. The clamping device 5, 6 of the described embodiment is comprised of two separate rows of base plates 3, 4 each supported by a respective chain link system that runs in tracks which are not shown in the Figures. As will be seen from FIG. 9, each base plate 3, 4 supports, via a support arm, a lever 7 which functions to clamp the edges of the web 1 firmly between itself and respective base plates 3, 4 through the action of a spring force. The levers 7 are self-locking, implying that the clamping force that holds the web 1 firmly to the base plates will increase as the material 1 is stretched in the transverse direction T. The clamping device is represented by arrows in FIG. 3.

Subsequent to the edges of the web 1 having been clamped firmly in the aforedescribed clamping device 5, 6, the tracks that guide the links in the chain link system diverge in the manner apparent from FIG. 1. The web 1 is thereby stretched successively in the transverse direction T. The links in the chain link systems then run parallel with one another and also parallel with the feed direction. In order to prevent the edges of the web 1 from being subjected to twisting forces as a result of directional changes of the base plates when entering and exiting those parts of the clamping device that are divergent and parallel relative to the feed direction, the levers 7 may be provided with abutment bodies 8, said bodies being rotatably carried at the abutment ends of the lever 7 and produced from a material that exhibits high friction to the material in the web 1. However, this is not normally necessary, since the flexible material to be stretched in the arrangement is able to take-up the small directional changes concerned relatively easily.

The clamping device 5, 6 may, for instance, be comprised of a chain link system from Flexlink, which includes two chains whose links carry the base plates 3, 4. In the illustrated case, each chain has a length of about 5 m and is provided with 75 base plates. The levers 7 on the base plates are normally closed and spring-biased. The length of chain may, of course, be chosen in accordance with requirements.

It will be understood that the invention is not restricted to the aforementioned stretching arrangement, and that other types of stretching arrangements may be used. For instance, there is described in EP-A1-0 443 244 a stretching arrangement that includes two wheels which are obliquely positioned in relation to each other and which are intended for stretching elastic film. The elastic film enters the wheels at a point where their mutual spacing is small and leaves the wheels at a point where their mutual spacing is large, therewith stretching the elastic film.

Figure 4:
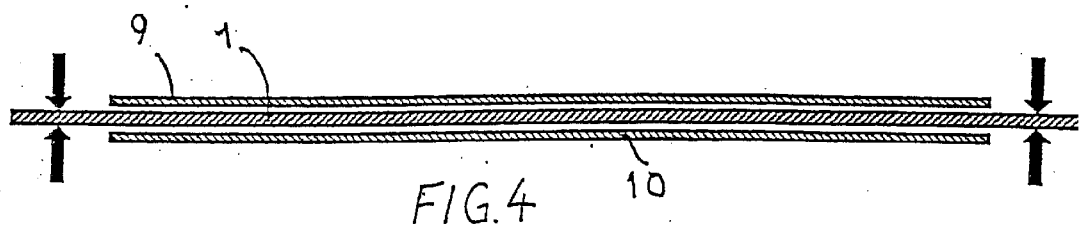

Subsequent to having stretched the web 1 to a desired extent, a web of material 9, 10 is applied to respective opposite sides of the web 1, as best seen from FIGS. 2 and 4.

The webs 1, 9, 10 then pass through an ultrasound welding unit 11 that includes a horn 12 and an anvil roll 13. The anvil roll 13 extends transversely across the combined webs of material and includes two regions of outwardly projecting anvils which are axially separated and symmetrically located relative to the longitudinal symmetry line A—A of the web 1. The anvils in these regions are comprised of axially separated rows of projections that extend peripherally around the circumference of the anvil roll 13. Thus, subsequent to having passed the ultrasound welding unit 11, the webs 1, 9, 10 are joined together in two mutually separate zones 14, 15 that extend in the feed direction, as evident from FIGS. 1 and 5. The ultrasound welding unit is conveniently driven in the manner described in EP-A1-0 494 941, so that the webs 9, 10 will be joined together through holes in the web 1. The manner in which welding is effected is well known to the person skilled in this art and will not therefore be described in more detail.

Figure 5:
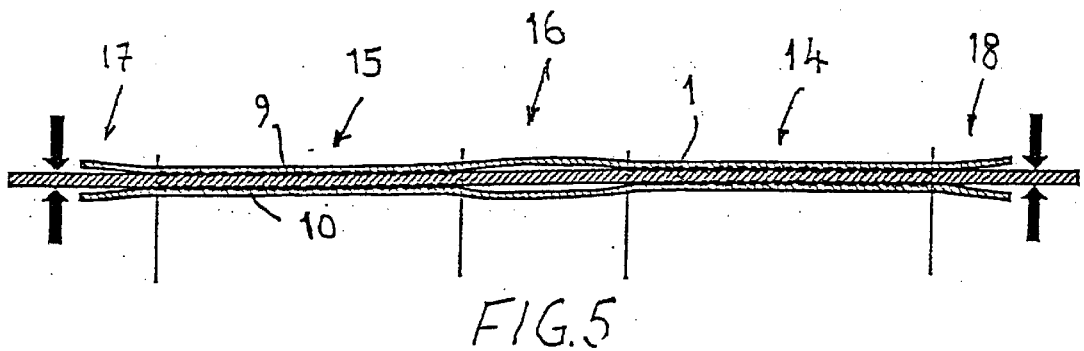

FIG. 5 illustrates the manner in which the sheets are joined together after having passed the ultrasound welding unit 11. The sheets are joined together over the whole of their respective surfaces, with the exception of a centre zone 16 and edge zones 17, 18. In the illustrated case, the width of the centre zone 16 corresponds to a third of the full width, whereas the edge zones 17, 18 correspond roughly to one-tenth of the full width. The width of the regions that shall be joined together will depend on the application concerned and will thus vary.

Figure 6:
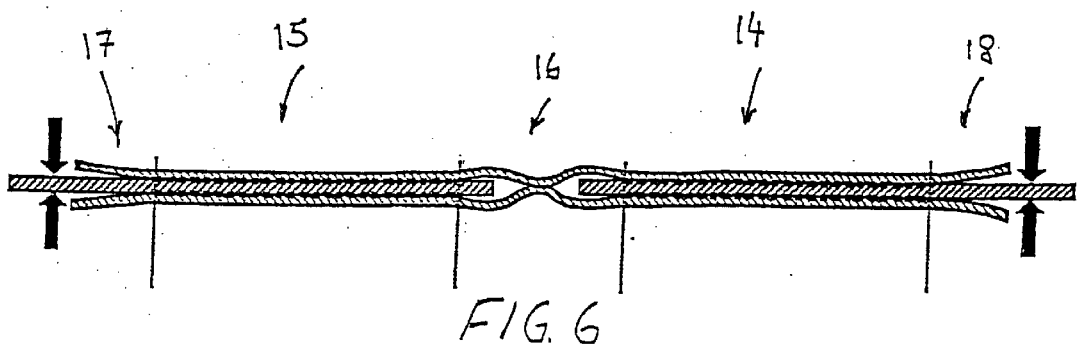
Figure 7:
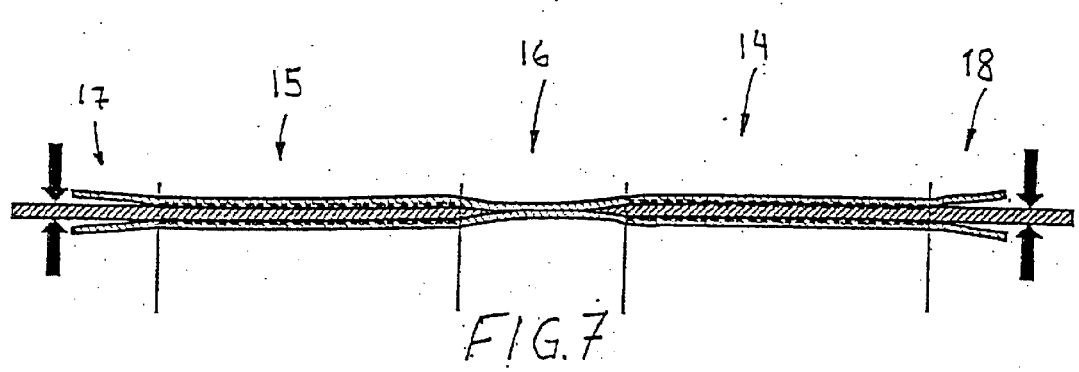

After having been joined together in the zones 14, 15 as they pass through the ultrasound unit 11, the webs 1, 9, 10 pass a dividing device 19. The dividing device 19 is comprised of an ultrasound welding unit that includes a horn 20 which coacts with an anvil roller 21 that includes outwardly projecting anvils 22 arranged in a semicontinuous pattern, as shown schematically in FIG. 10. By semicontinuous pattern is meant here a surface whose topography is so configured that one point across the width of the pattern will always abut the ultrasound horn, whereas any chosen peripheral circumference line will exhibit discontinuous abutment with the ultrasound horn. Patterns of this type can be produced, for instance, with a knurling process, although other manufacturing processes may be used, such as milling, sparking or etching. The pattern is adapted to the desired perforation of the web 1 and so that the distance between adjacent perforations will be so small as to enable the elastic force in the stretched web 1 to pull the web apart in each region between two perforations. The perforations are formed as the three webs 1, 9, 10 move together through the gap or nip between the horn 20 and the outwardly projecting anvil 22. Ultrasound energy is transmitted to the three webs 1, 9, 10 at those points where the semicontinuous pattern 22 lies against the ultrasound horn 20. Because the intermediate web 1 is elastic and is in a stretched state, the amount of ultrasound energy that the web can store is smaller than the amounts of energy that can be stored by the non-loaded webs 9 and 10 on respective sides of said intermediate web 1, meaning that the ultrasound welding unit can be operated so as to perforate solely the intermediate, stretched web 1. As the elastically stretched web 1 absorbs the energy to which it is subjected by the up and down movements of the ultrasound horn, two different phenomena can cause the web to rupture locally. There either occurs a local rise in temperature that softens the elastic web 1 and the tensile force in surrounding parts of the web draw-in towards themselves softened material so as to create a perforation. Alternatively, the ultrasound energy assists in causing the material in the elastic and stretched web 1 to become brittle as a result of so-called visco-elastic inertia, and thereby rupture at the point of perforation. A combination of these phenomena is, of course, also conceivable. The webs 9, 10 are also subjected to ultrasound energy in conjunction with perforation of the web 1. The webs 9, 10, however, are not subjected to load and are therefore able to absorb more of the energy delivered without rupturing. However, these webs will also be softened by the ultrasound energy delivered and therewith be joined together in the perforation openings of the web 1 immediately after said openings have been formed in the aforedescribed manner. Because the distance between mutually adjacent perforations is small, the material in the elastic web 1 between the latest created openings and nearest preceding openings will be torn apart by the tensile force in the stretched elastic material immediately after the opening has been formed. Subsequent to having been divided, the web 1 will contract within the centre zone 16 to a totally relaxed state, which means that a large central part of the centre zone 16 will consist solely of two sheets or layers subsequent to said division. FIG. 6 is a schematic illustration of the webs 1, 9, 10 subsequent to their passage through the dividing device 19.

Alternatively, the anvil pattern on the anvil roll may be discontinuous instead of semicontinuous. It is also possible to use a fully continuous pattern, although in this latter case there is a serious risk of the webs 9, 10 also being divided, as these webs are subjected to the tensile force in the elastic web 1 in those zones 14, 15 in which the three webs are mutually joined, subsequent to division of the web 1. It is therefore preferred to use an anvil roll that has a semicontinuous anvil pattern.

It will be understood that much less energy is required to perforate the stretched elastic web 1 than that consumed in perforating the webs 9, 10. The amount of energy consumed in perforating the web 1 will depend on the choice of elastic material and the extent to which the elastic material is stretched. Thus, it is possible to drive the dividing device 19 so that the energy delivered to the webs 9, 10 will not be high enough to cause local melting of these webs in the division process but sufficiently high to cause perforation of the elastic web 1, wherewith the webs 9, 10 remain unconnected with each other subsequent to dividing the elastic web 1.

Subsequent to the webs 1, 9, 10 have passed the dividing device 19, they pass an ultrasound welding unit 22 positioned in the centre zone 16. This unit includes a horn 23 that coacts with an anvil roll 24 which includes outwardly projecting anvils that are conveniently comprised of peripheral rows of projections so as to achieve punctiform welding of the centre zone 16. The unit 22 shall be placed at a distance from the dividing device 19 such that the parts of the web 1 situated in said centre zone will have had time to contract fully before the webs 1, 9, 10 are joined together in the centre zone 16. Subsequent to having passed the unit 22, the webs 1, 9, 10 will be joined together also in the centre zone, as shown schematically in FIG. 7.

Subsequent to this joining of the webs 1, 9, 10 in the centre zone, the tracks carrying the chain links converge towards each other, therewith causing the edges of the webs to be moved closer to each other and therewith allow the web 1 to contract in the zones 14, 15 in which the web 1 is still stretched, and in the edge zones 17, 18. Contraction of the web 1 in the zones 14, 15 causes the webs 9, 10 to be pleated into soft folds. When the distance between the edges has reduced to such an extent that the web 1 is moved in a generally relaxed state with no tension, the levers 7 of the clamping device are caused to swing upwards and therewith release the edges of the web 1.

Figure 8:
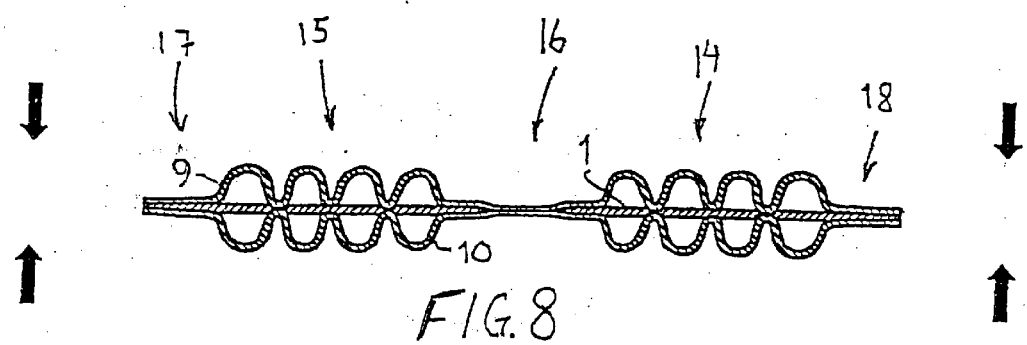
Figure 9:
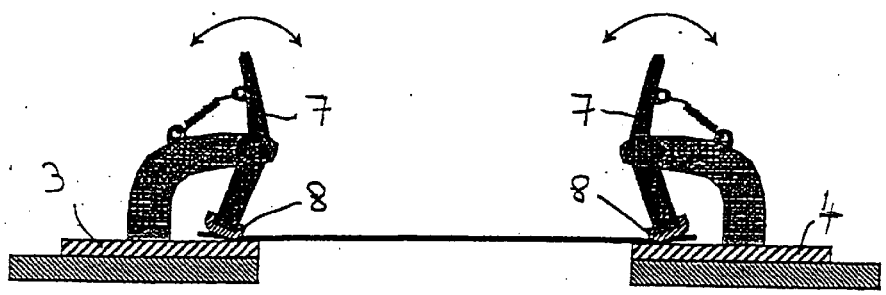
FIG. 9 is a cross-sectional view of devices for firmly holding a web of elastic material included in the arrangement shown in FIG. 1.
Figure 10:
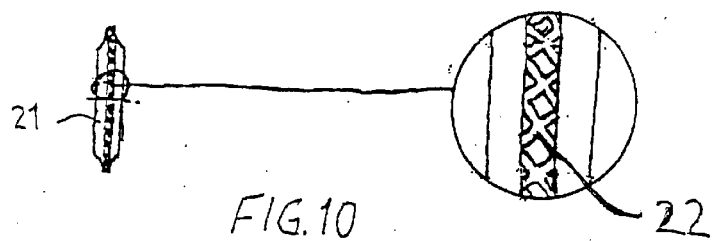
FIG. 10 illustrates a counterpressure or anvil roller in a web dividing device included in the arrangement shown in FIG. 1.

In the case of the embodiment illustrated in the Figures, the webs 1, 9, 10 are then joined together in the edge zones 17, 18 by means of an ultrasound welding unit 25 and the webs will have the configuration shown in FIG. 8 after having passed the unit 25. Should it be found that after being released by the levers 7 those parts of the web 1 situated in the edge zones do not contract to an extent sufficient for said parts to lie flush with or inwardly of the outer edges of the webs 9, 10, the laterally outward projecting parts of the web 1 are suitably cut away. Edge welding is not absolutely necessary, since the mutually joined webs are intended to be used in the manufacture of fastener tabs, wherewith the edge zones 17, 18 form those parts of the tabs that are fixed permanently to absorbent articles, meaning that the sheets or layers of material can be mutually joined in said edge zones in conjunction with fastening such a tab to an absorbent article.

Welding of the centre zone 16 can alternatively be effected after the web 1 has been caused to relax to a tensionless state and its edges released, therewith enabling edge and centre welding to be effected simultaneously.

Neither is it absolutely necessary to control contraction of the web 1 subsequent to joining together the webs in said centre zone, since the clamping device can be constructed to release the edges of the web immediately after the webs have been joined in the centre zone. Abrupt release of the webs, however, may cause the composite web formed by said three webs to be pleated or puckered in an undesirable fashion and is therefore not preferred.

As the mutually joined webs 1, 9, 10 leave the aforedescribed arrangement, the webs are rolled onto a storage reel 26 or transferred to a process line in which absorbent article fastener tabs are produced from the basic starting material manufactured in the aforedescribed arrangement, said process line possibly being integrated with a process line for the manufacture of absorbent articles.

Such a process line may include, for instance, the application of mutually separated and longitudinally extending strings of male or female elements, such as strings of hook elements in a so-called touch-and-close fastener, whereafter mutually opposing fastener tabs are cut from the thus formed web in pairs.

Figure 11:
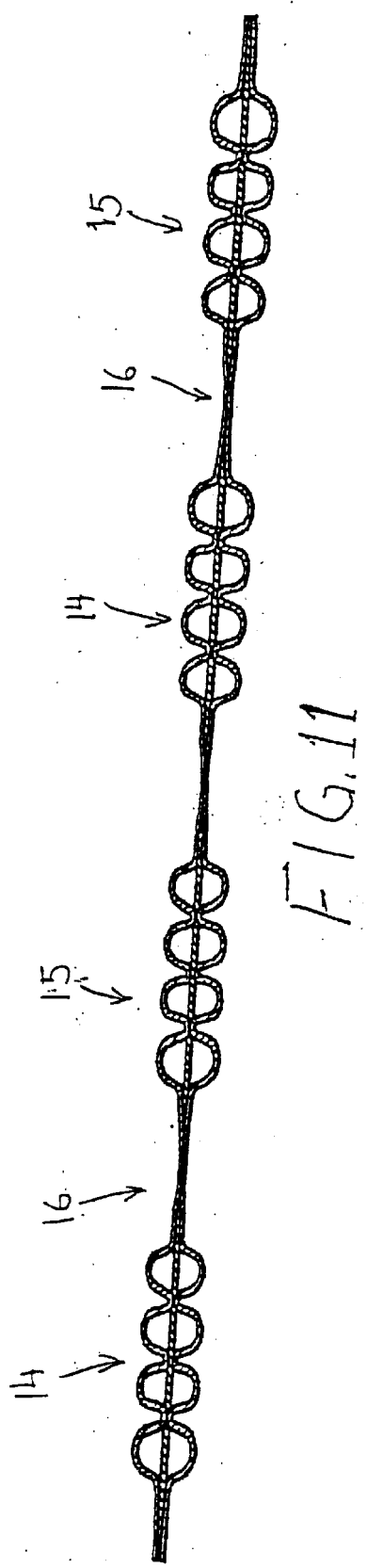
FIG. 11 illustrates another embodiment of a basic starting material according to the invention.

It will be understood that the inventive arrangement may include more dividing devices and welding units than those inferred above, so as to enable more elastic zones corresponding to zones 14–16 to be formed. In such arrangements, it may be suitable to support the webs at their outer edges so as to ensure that the composite web will not move laterally as the stretched web is divided in each region between two elastic zones. Such supports may have the form of wheels or co-running belts. FIG. 11 is a cross-sectional view of a web of material that has four zones corresponding to the zones 14, 15 and three zones corresponding to the centre zone 16. Such a web can then be divided into two webs corresponding to the web manufactured by means of the inventive arrangement illustrated in FIGS. 1–10.

Figure 12:
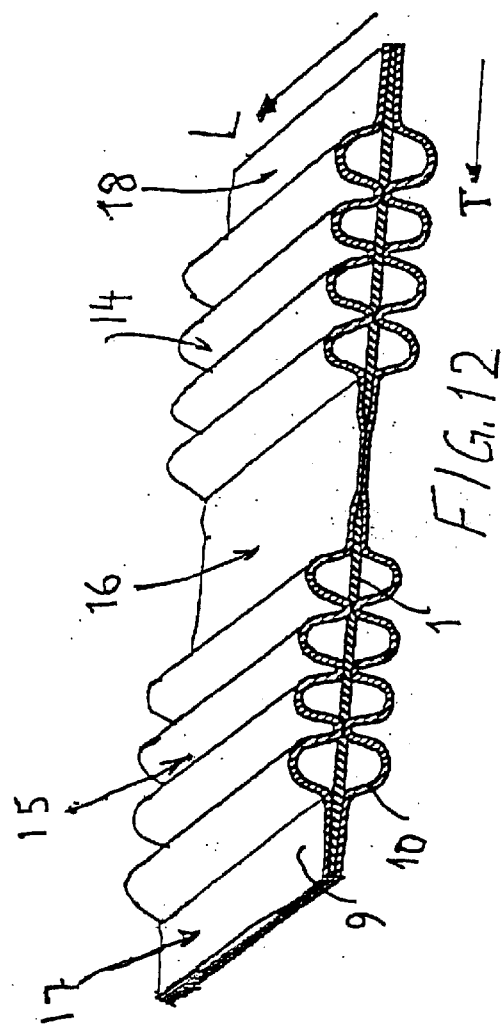
FIG. 12 illustrates a first embodiment of an inventive basic starting material produced with the arrangement shown in FIGS. 1–10.

FIG. 12 illustrates schematically and in perspective a section of basic starting material intended for the manufacture of absorbent article fastener tabs and produced by means of the arrangement shown in FIGS. 1–10, said starting material having a length L, a cross width T, two elastic sheets 1 and at least two further sheets 9, 10, which are preferably comprised of nonwoven material. The sheets 1, 9, 10 are joined together in the aforedescribed manner, such as to form two zones 14, 15, two edges 17, 18 and a centre zone 16. The zones 14, 15 are elastic in the cross-direction T, whereas remaining zones are non-elastic, by virtue of the fact that the sheets 9, 10 are comprised of a generally unstretchable material. The relationship between transversal extension of the elastic zones in a maximum stretched state and in a relaxed state is less than or equal to the ratio of the transverse extension of the intermediate non-elastic zone to the sum of the transverse extension of those pieces of elastic material that extend into said zone, since the elastic material is able to contract freely in the non-elastic zone while part of the force for contracting the non-elastic sheets 9, 10 is consumed in the elastic zone, and consequently the elastic material will remain somewhat stretched in the elastic zone.

Figure 13:
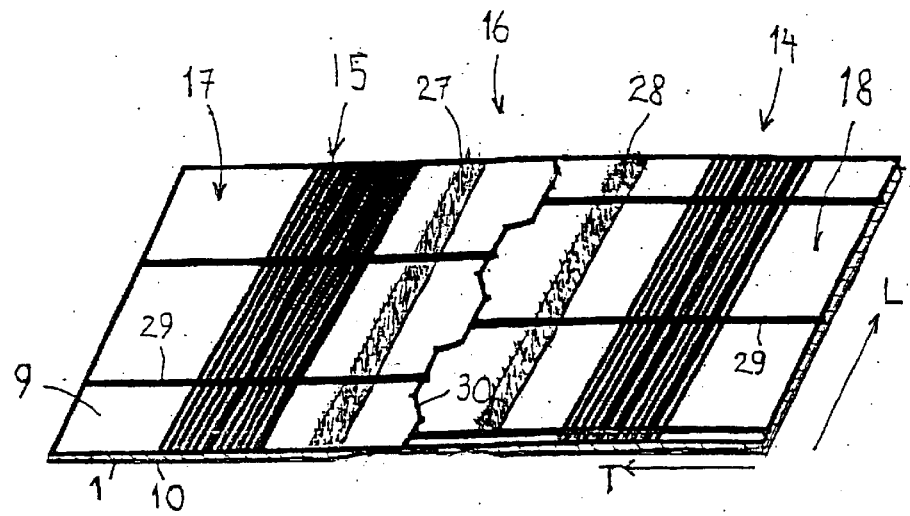
FIG. 13 is a schematic illustration of the manufacture of fastener tabs from the material shown in FIG. 12.

Fastener tabs can be produced readily from the basic starting material, by fastening longitudinally extending and mutually separated strings 27, 28 of hook elements onto the material in the centre zone 16, and thereafter cutting right-hand and left-hand fastener tabs from the material. FIG. 13 shows schematically how fastener tabs can be cut-out so as to enable the starting material to be used without any appreciable wastage. The material is first cut along a line 30 that has a modified square-wave shape and which extends in the longitudinal direction L of the starting material in the centre of the zone 16, whereafter cuts are made along a sequence of cutting lines 29 that extend in the cross-direction T of said material from said respective edges thereof up to the longitudinal line 30, such that each line 29 intersects a wave crest or wave trough of the undulating line 30 in its centre. The cutting lines 29 on respective sides of said longitudinal line 30 are offset relative to each other through a distance corresponding to one half wavelength, so that the sequence of cutting lines 29 on one side of the cutting line 30, e.g. the right-hand side in the Figure, each intersect wave crests, whereas the cutting lines on the other side of the cutting line 30, the left-hand side in the Figure, each intersect wave troughs. As will be seen from FIG. 13, pairs of left-hand and right-hand fastener tabs will be cut from the starting material in this way, wherewith the tabs in each pair of tabs are offset relative to one another in the longitudinal direction of said material.

It is, of course, possible to use other regular wave shapes for the cutting line 30, e.g. a sinusoidal wave or a purely square wave shape.

Figure 14:
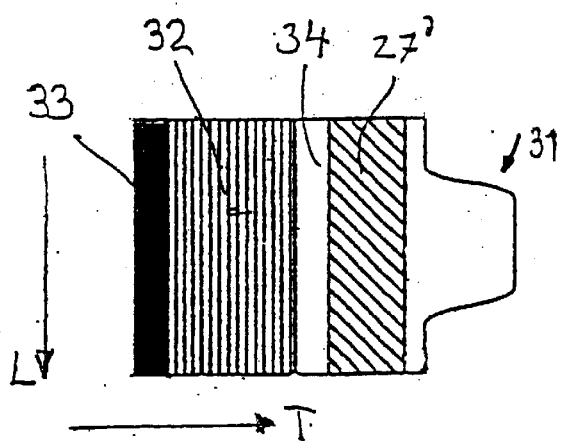
FIG. 14 illustrates a fastener tab according to one embodiment of the invention.

FIG. 14 illustrates schematically one such fastener tab 31 which has a continuous layer of material that includes a central elastic part 32 and two non-elastic parts 33, 34, of which the part 33 is the manufacturer-end of the tab 31 and is intended for attachment to one side portion of an absorbent article, such as a diaper. The other non-elastic part 34 is located at the user end of the tab, i.e. the end of the tab which is gripped by the wearer in order to fasten together the side portions of a donned diaper. The central elastic part 32 is formed so as to be elastic in the transverse direction T and essentially non-elastic in the longitudinal direction L.

The non-elastic part 34 is conveniently provided with some form of fastener elements 27', particularly such that can be "firmly locked" and then "unlocked". Examples of suitable fastener elements include male or female parts of touch-and-close fasteners, buttons, or the like, which are intended to coact with complementary elements provided on the outside of the diaper. It is also possible to use adhesive or cohesive binding agents as fastener elements.

Diapers often include an outer sheet of nonwoven material to which certain types of hook elements can readily fasten, and it is therefore beneficial to use fastener elements 27' in the form of such hook elements. It is also possible to provide the diaper with special loop elements to which the fastener elements 27' can be coupled.

Although the fastener tabs 31 have been shown to have a generally rectangular shape, it will be understood that the tabs may have any other suitable shape.

Although the invention has been described above with reference to a diaper, it will be understood that the invention is not restricted thereto and can be applied with any type of absorbent article whatsoever.

In order to provide the wearer of the diaper with a high degree of comfort, it is suitable for the fastener tabs to have a given stiffness, particularly in the longitudinal direction L. It is also important that the tabs will not chafe the wearer. The non-elastic material is suitably chosen so that the laminate will have sufficient stiffness while, at the same time, being soft and gentle against the wearer's skin. This material will preferably be a nonwoven material.

An example of suitable non-elastic material is 20 grams spunbond (nonwoven) and 30 grams spunbond (nonwoven) as material layers, preferably two nonwoven layers containing thermoplastic fibres, e.g. polypropylene fibres.

The thinner nonwoven layer (20 grams) is softer and is placed suitably against the wearer's skin. The thicker layer (30 grams) provides stiffness. The use of different thicknesses enables the fastener tabs to bend when applied to an absorbent article. The fastener tab folds automatically towards the thinner nonwoven layer, by virtue of the fact that the elastic layer disposed between the nonwoven layers and mounted in a stretched state is able to contract more to that side on which the thinnest layer of nonwoven is fastened. The fastener element 27' will therefore preferably be fastened to the thinnest nonwoven layer. This is beneficial when the fastener tab shall be secured to the diaper and folded in towards/against the inside of said diaper.

The elastic layer or sheet 1 may consist of elastic film, elastic foam, elastic net material or of a laminate that includes at least one elastic component.

Figure 15:
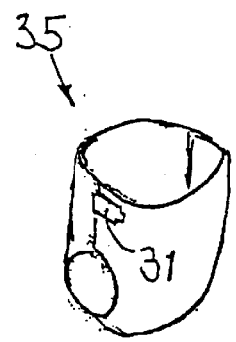
FIG. 15 is a schematic illustration of a diaper provided with inventive fastener tabs.

FIG. 15 illustrates schematically a diaper 35 whose side portions have been fastened together with the aid of fastener tabs 31 of the kind shown in FIG. 14.

Absorbent articles normally include a surface sheet, an acquisition/transport sheet, a rear liquid-impermeable sheet, or backing sheet, and an absorbent body. The acquisition/transport sheet may be comprised of a high loft material. The absorbent body of such products may be made of cellulose pulp. These layers or sheets will not be described in more detail, since they are well known to the person skilled in this art.

It will be understood that the described embodiments can be modified in several ways within the scope of the invention. For instance, the anvil roll 13 may be comprised of two or more separate rolls that each coact with its individual ultrasound horn. Moreover, joining of the webs in the different zones, and for thermoplastic materials also the division of the stretched web 1, may be effected by means of heat welding units instead of ultrasound welding units. Heat welding can be accomplished with the aid of a high mechanical pressure in addition to heated rollers or the like. The webs may also be joined together with the aid of gluing units instead of ultrasound welding units. Furthermore, there may be used anvil patterns other than the described rows of projections, and it is also possible to use patterns other than a semicontinuous pattern on the anvil roller in the dividing device. Although it is preferred to use essentially non-stretchable material in the material webs to which the stretched web is joined, it will be understood that it is also possible to use elastic material in these webs instead when wishing to produce material that has different degrees of elasticity in different zones. Although the elastic web is divided centrally between the elastic zones in the illustrated embodiment, it will be understood that the dividing line may be placed closer to one elastic zone than to the other. The invention is therefore restricted solely by the contents of the accompanying Claims.

What is claimed is:

1. A method of producing basic starting material for the manufacture of fastener tabs (31) intended for joining side portions of front and rear parts of an absorbent article that includes a front part, a rear part and an intermediate crotch part, so as to give the article a pants configuration, which comprises the steps of stretching a first sheet (1) of elastic material in a first direction (T);

applying a second and a third sheet of material (9, 10) onto respective opposite sides of the first sheet;

fastening the three material sheets together in at least two mutually separated zones (14, 15) that extend parallel with each other in second direction (M) perpendicular to said first direction;

dividing the first sheet (1) in a central region between the two zones (14, 15) along a line that lies between said zones, whereby the first sheet in said central region (16) between the two zones (14, 15) contracts to a non-stretched state, and thereafter fastening the three sheets together in the central region (16) between the two zones (14, 15).

2. The method according to claim 1, characterised by fastening the sheets of material (1, 9, 10) to each other in the central region (16) between the two zones (14, 15) in which the second and third sheets (9, 10) are fastened to said first sheet (1) with said sheet in a stretched state and with said first sheet (1) stretched in said zones.

3. The method according to claim 1, characterised by causing the first sheet (1) to contract to a non-stretched or relaxed state prior to fastening said sheets (1, 9, 10) together in he central region (16) between the two zones (14, 15) in which the second and third sheets (9, 10) are fastened to the first sheet (1) with said sheet in a stretched state.

4. The method according to claim 2, characterized by joining the first, second and third sheets (1, 9, 10) together with two edge regions (17, 18) that extend in said second direction (M) and that extend in said first direction (T) outwardly of he nearest zone (14, 15) in which the second and third sheets (9, 10) are joined to the first sheet (1) with said sheet in a stretched state subsequent to having caused the first sheet to contract to a non-stretched state in the zones (14, 15) in which the second and third sheets (9, 10) are joined to the first sheet (1) with said sheet in a stretched state.

5. The method according to claim 2, characterized by dividing the first sheet (1) in the central region between the two zones (14, 15) in which the second and third sheets (9, 10) are joined to the first sheet (1) with said sheet in a stretched state through the medium of a line of perforations produced in the first sheet, wherein the distance between said perforations is so small as to enable the contraction force in the stretched first sheet of material to pull said first sheet apart in the region between two mutually sequential perforations.

* * * * *